(12) United States Patent
Kranz (10) Patent No.: US 11,513,090 B2
(45) Date of Patent: Nov. 29, 2022

(54) APPARATUS AND METHOD FOR EVALUATING THE QUALITY OF AT LEAST ONE SOLDER JOINT BETWEEN A PRINTED CIRCUIT BOARD AND A CURRENT SENSOR

(71) Applicant: Infineon Technologies AG, Neubiberg (DE)

(72) Inventor: Theodor Kranz, Sirnitz (AT)

(73) Assignee: Infineon Technologies AG, Neubiberg (DE)

( * ) Notice: Subject to any disclaimer, the term of this patent is extended or adjusted under 35 U.S.C. 154(b) by 123 days.

(21) Appl. No.: 16/993,544

(22) Filed: Aug. 14, 2020

(65) Prior Publication Data

US 2021/0063335 A1   Mar. 4, 2021

(30) Foreign Application Priority Data

Sep. 3, 2019   (DE) .......................... 102019123582.0

(51) Int. Cl.
*G01N 27/04*   (2006.01)
*G01N 33/207*   (2019.01)

(52) U.S. Cl.
CPC ......... *G01N 27/041* (2013.01); *G01N 27/046* (2013.01); *G01N 33/207* (2019.01)

(58) Field of Classification Search
CPC .. G01N 27/041; G01N 27/046; G01N 33/207; G01R 15/207; G01R 31/71; G01R 35/00
See application file for complete search history.

(56) References Cited

U.S. PATENT DOCUMENTS 3,192,474 A * 6/1965 Cherry ..................... G01N 3/00
                                                     228/104

FOREIGN PATENT DOCUMENTS

| DE | 112175 A1 | 3/1975 | |
| DE | 102012110280 A1 * | 5/2013 | ........... H01M 10/48 |
| DE | 102015217182 A1 | 3/2017 | |
| JP | 5420461 B2 * | 2/2014 | |
| SU | 1609565 A1 * | 11/1990 | |

* cited by examiner

*Primary Examiner* — Jay Patidar
(74) *Attorney, Agent, or Firm* — Harrity & Harrity, LLP (57) ABSTRACT

The present disclosure relates to a concept for checking at least one solder joint between a printed circuit board and a current sensor, including: measuring, by means of the current sensor, an electric current through the solder joint; measuring at least one temperature of the current sensor as a function of the electric current; and ascertaining a quality of the solder joint based on the temperature and the electric current.

23 Claims, 4 Drawing Sheets

APPARATUS AND METHOD FOR EVALUATING THE QUALITY OF AT LEAST ONE SOLDER JOINT BETWEEN A PRINTED CIRCUIT BOARD AND A CURRENT SENSOR

RELATED APPLICATION

This application claims priority to German Patent No. 102019123582.0 filed on Sep. 3, 2019, which is incorporated herein by reference in its entirety.

FIELD

The present disclosure relates to apparatuses and methods for checking at least one solder joint between a printed circuit board and a current sensor.

BACKGROUND

Electrification in the automotive sector and industrial automation are pushing current measurement increasingly into the foreground. Specifically, applications directed at high power density require current sensors that can easily be mounted on printed circuit boards. In a design in which a current sensor is soldered to a printed circuit board, the solder joint quality needs to be as good as possible in order to avoid power losses as a result of poor conductivity between for example a busbar and a current sensor.

A readily conductive, cavity-free solder joint is therefore important in order to ensure as low an additional resistance as possible. Poor solder joints containing cavities can influence the accuracy and sensitivity of the current sensor. A typical current range for low resistance current sensors on a printed circuit board is between 0 and 120 A. Especially in the case of high current applications such as 50 ARMS (RMS=root mean square), it is important for an insertion resistance arising as a result of a current sensor being inserted into a circuit to be kept low in order to avoid power losses in the system. For reasons of reliability too, it is necessary to ensure good solder joints containing fewer cavities and high conductivity between sensor pads and the sensor surface in the system. It is therefore recommended that the quality of the solder joint be confirmed.

For low-voltage logic pins, which are not as large as current-carrying power pins, solder point verification can be performed using function tests. However, the solder joint of the power pins or high current pins needs to be checked in order to ensure high conductivity and fewer solder cavities.

The quality of a solder joint for wireless sensors can be checked by means of x-rays (x-ray inspection) or by means of automated optical inspection (AOI), for example. X-ray inspection for every soldered part is not always feasible on account of the high level of complexity and the more acute effects of cost. AOI requires the device to be equipped with a lead tip inspection (LTI) function in order to allow partial or complete coating of a connection tip. The wettable coating of the connection tip allows AOI after soldering, but also increases production costs.

There is therefore a need for further options for checking a solder joint between a printed circuit board and a current sensor.

SUMMARY

This is achieved by apparatuses and methods according to the independent claims. Advantageous developments are the subject of the dependent claims.

According to a first aspect of the present disclosure, a method for checking at least one solder joint between a printed circuit board and a current sensor is proposed. The current sensor is used to measure an electric current through the solder joint. Further, at least one temperature of the current sensor is measured as a function of the electric current. A quality of the solder joint is ascertained based on the temperature and the electric current.

The measurement of the current flowing through the current sensor and the measurement of the temperature in or on the current sensor can involve a power loss being rated by an algorithm that takes into consideration both pieces of information. On the basis of a current-dependent thermal rating in a sensor package, a useful statement can be made about a quality of a solder point or a conductivity. The information about the quality of the solder point can be forwarded from the current sensor to its surroundings. Depending on prescribed limit values (for temperature and current), a user can obtain confirmation of the solder point.

According to some exemplary embodiments, the temperature is measured by means of a temperature sensor integrated in the current sensor. Current sensors often also include temperature sensors jointly integrated in a package of the current sensor. This can be exploited in order to avoid separate temperature sensors and/or to render the temperature measurement more accurate.

According to some exemplary embodiments, the current intensity and the duration of the electric current are predetermined or preset for checking the solder joint. The current through the solder joint can thus be impressed (applied) at a current intensity within a predetermined range regardless of the quality of the solder joint. Depending on the quality of the solder joint, a temperature or temperature profile will then be obtained. If the quality of the solder joint is low, higher temperatures can be expected in principle than for readily conductive solder joints of higher quality.

According to some exemplary embodiments, the measuring of the temperature includes the measuring of a temperature gradient. The quality of the solder joint is then ascertained based on the temperature gradient and the electric current. For example, an algorithm can take into consideration the temperature gradient for the measurement of the current (or of the magnetic field caused by the current). If the temperature exceeds a preset limit value while a preset current range is being monitored, the sensor can indicate the infringement. This algorithm can be effected either by using preset lookup tables or by comparing the measured current and temperature values with a few preset limit values.

According to some exemplary embodiments, a first temperature of the current sensor is measured before the electric current is impressed, and a second temperature of the current sensor is measured at the end of the electric current being impressed. The temperature gradient can be ascertained based on the first and second temperatures and a period of time for which the electric current is impressed.

According to some exemplary embodiments, the ascertaining of the quality of the solder joint involves the measured temperature being compared with temperatures ascertained for the electric current and for different solder joint qualities beforehand. The use of such a lookup table allows efficient rating of the solder joint quality to take place.

According to some exemplary embodiments, the quality of the solder joint is ascertained by means of a processor integrated with the current sensor. An external processor requiring additional space and/or circuitry can therefore be dispensed with.

According to some exemplary embodiments, the measured electric current and the measured temperature are conveyed from the current sensor to an external processor via an interface, whereupon the external processor can take this as a basis for ascertaining the quality of the solder joint. Exemplary embodiments of this kind might be possible when the current sensor does not have a suitable internal processor.

In principle, the current sensors used can be sensors based on a wide variety of principles. By way of example, the current sensor can include at least one Hall sensor and/or a magnetoresistive (e.g. AMR, GMR, TMR) sensor.

According to a further aspect of the present disclosure, an apparatus for checking at least one solder joint between a printed circuit board and a current sensor is proposed, wherein the current sensor is designed to measure an electric current through the solder joint and at least one temperature of the current sensor as a function of the electric current, wherein the apparatus includes a processor for ascertaining a quality of the solder joint based on the temperature and the electric current.

The processor can include a processor that is external to the current sensor, and the current sensor and the processor can be connected via a signal interface for transmitting signals that indicate the measured temperature and the electric current. On the other hand, the processor and the current sensor can also be in the form of an integrated circuit.

BRIEF DESCRIPTION OF THE DRAWINGS

A few examples of apparatuses and/or methods are illustrated in more detail merely by way of example below with reference to the accompanying figures, in which.

DETAILED DESCRIPTION

Various examples are now described more thoroughly with reference to the accompanying figures, which depict a few examples. The thicknesses of lines, layers and/or regions in the figures may be exaggerated for clarification purposes.

While further examples are suitable for various modifications and alternative forms, some specific examples thereof are accordingly shown in the figures and are described thoroughly below. However, this detailed description does not restrict further examples to the specific forms described. Further examples can cover all modifications, counterparts and alternatives that fall within the scope of the disclosure. Throughout the description of the figures, identical or similar reference signs refer to identical or similar elements that can be implemented identically or in modified form in comparison with one another, while they provide the same or a similar function.

It goes without saying that if one element is referred to as "connected" or "coupled" to another element, the elements can be connected or coupled directly or via one or more intermediate elements. If two elements A and B are combined using an "or", this should be understood such that all possible combinations are disclosed, i.e. only A, only B, and A and B, unless explicitly or implicitly defined otherwise. An alternative wording for the same combinations is "at least one of A and B" or "A and/or B". The same applies, mutatis mutandis, to combinations of more than two elements.

The terminology used here to describe specific examples is not intended to have a limiting effect for further examples. When a singular form, for example "a, an" and "the" is used, and the use of only a single element is defined neither explicitly nor implicitly as obligatory, further examples can also use plural elements in order to implement the same function. If a function is described below as implemented using multiple elements, further examples can implement the same function using a single element or a single processing entity. Furthermore, it goes without saying that the terms "comprises", "comprising", "has" and/or "having" in their usage specify the presence of the indicated features, integers, steps, operations, processes, elements, components and/or a group thereof, but do not exclude the presence or addition of one or more other features, integers, steps, operations, processes, elements, components and/or a group thereof.

Unless defined otherwise, all terms (including technical and scientific terms) are used here in their customary meaning in the field with which examples are associated.

Figure 1A:
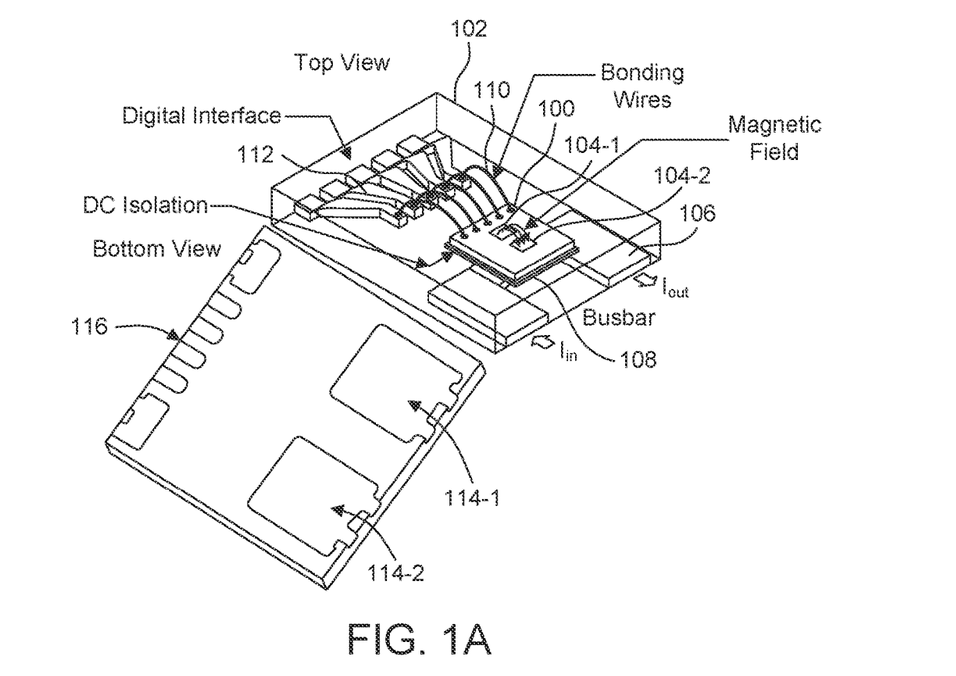
FIG. 1A shows an example of a current sensor package.

FIG. 1A shows an exemplary integrated magnetic field sensor circuit 100 in a package 102 both in plan view and in a view from below. By measuring a magnetic field, it is then possible to infer a current causing the magnetic field, as a result of which the magnetic field sensor circuit is also referred to as a current sensor below.

The magnetic field sensor circuit or the current sensor 100 in this instance comprises differential Hall sensors 104-1, 104-2 arranged above a current-carrying line 106 inside the package 102. Between the Hall sensors 104-1, 104-2 and the current-carrying line 106, there is provision for a DC isolation 108. The current sensor 100 is connected inside the package 102 to an interface 112 by means of connecting lines 110, in order to couple the current sensor 100 to further components, such as for example an external processor. On an underside of the sensor package 102, there is provision for connection pads 114-1, 114-2, in order to connect the current-carrying line 106 to an external current-carrying line (not shown in FIG. 1A), such as e.g. a busbar. Further, connection pads 116 are shown, in order to connect the interface 112 to further components. The connection pads 114-1, 114-2, 116 of the sensor package 102 can be soldered to a printed circuit board (not shown in FIG. 1A), for example. This is shown schematically in FIG. 1B. The term "current sensor" is also used generally below to denote the packaged sensor circuit of FIG. 1A, that is to say a current sensor in a package, and can comprise further circuit components in the package.

Figure 1B:
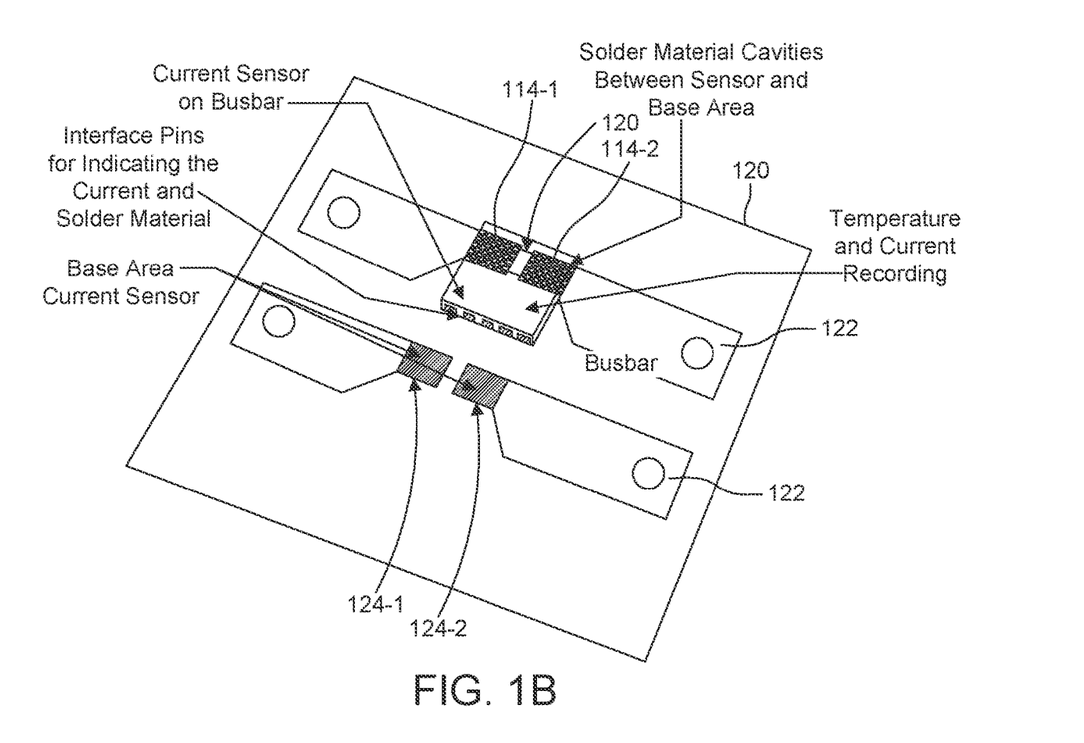
FIG. 1B shows an example of a current sensor footprint and a current sensor soldered to a printed circuit board (busbar)

FIG. 1B shows a printed circuit board 120 without (bottom) and with (top) a soldered-on sensor package 102.

The printed circuit board 120 comprises a conductor track or a busbar 122. At a point envisaged for the current sensor, the busbar 122 is interrupted and has connection pads 124-1, 124-2 corresponding to the connection pads 114-1, 114-2. The connection pads 114-1, 114-2 of the sensor package 102 can be soldered to the connection pads 124-1, 124-2 of the printed circuit board 120, in order to connect the current sensor to the busbar 122. A solder joint is therefore produced between the printed circuit board 120 and the current sensor 100. The present disclosure is concerned with a concept for testing such solder joints.

Figure 2A:
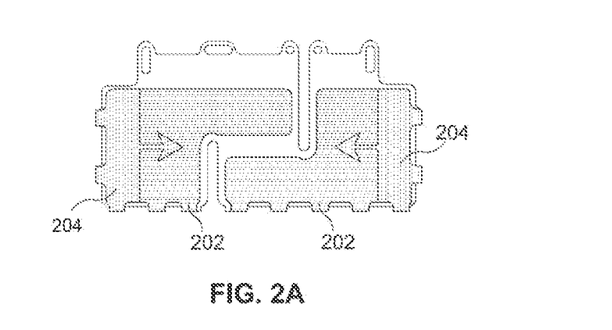
FIGS. 2A and 2B show examples of solder cavities.
Figure 2B:
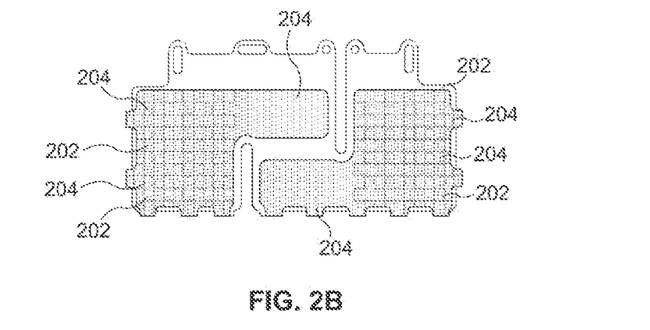

FIGS. 2A and 2B schematically show different solder joints between the connection pads 114 and 124 having different conductivities. FIG. 2A shows a solder joint having predominantly regions 202 of high conductivity (no cavities). The regions 202 represent an intact, conductive solder point between the current-carrying line 106 and the printed circuit board 120. Regions of low conductivity (for example on account of cavities) are denoted by the reference sign 204. By contrast, FIG. 2B shows a relatively poorly conductive solder joint on account of numerous regions 204 of low conductivity (cavities, also referred to as voids or solder voids). The regions 204 represent a nonconductive solder point between the current-carrying line 106 and the printed circuit board 120.

Too many cavities 204 in the solder joint between the busbar and the current sensor mean that a temperature rise when a current flows through the solder joint can exceed limit values required in the system. An effective sensitivity of the current sensor can also change after the current sensor is soldered on, since a poor solder joint reduces the conductivity of the solder joint, which hampers the flow of current through the current sensor. The poor conductivity means that the power loss in the high current path 106, 122 increases.

Figure 2C:
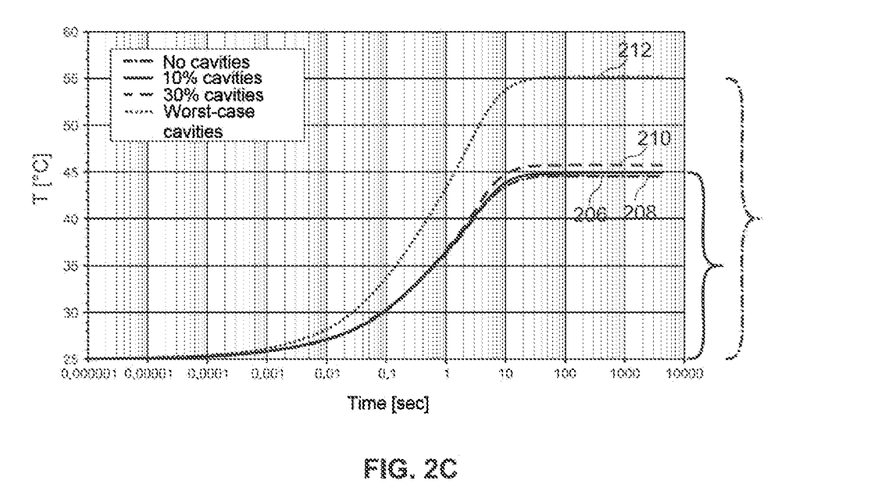
FIG. 2C shows qualitatively different temperature rises for different proportions of regions of low conductivity in a solder joint.

FIG. 2C shows qualitatively different temperature rises for different proportions of regions 204 of low conductivity in a solder joint.

Curve 206 represents a temperature rise in or on the current sensor in the case of a perfect solder joint without cavities while a current of a specific RMS current intensity flows through the busbar (sensor package). Curve 208 represents a temperature rise on the current sensor in the case of a solder joint with a 10% cavity proportion. Curve 210 represents a temperature rise on the current sensor in the case of a solder joint with a 30% cavity proportion. Curve 212 represents a temperature rise on the current sensor in the case of a poor solder joint with a high cavity proportion. While the temperature rises 206, 208, 210 differ only slightly, the temperature rise 212 is markedly different at the top. The present disclosure allows such worst-case scenarios to be identified. FIG. 2C shows an example in which a sensor temperature of in the worst case 55° C. arises on account of solder cavities. This limit can be used to indicate poor conductivity.

Figure 3:
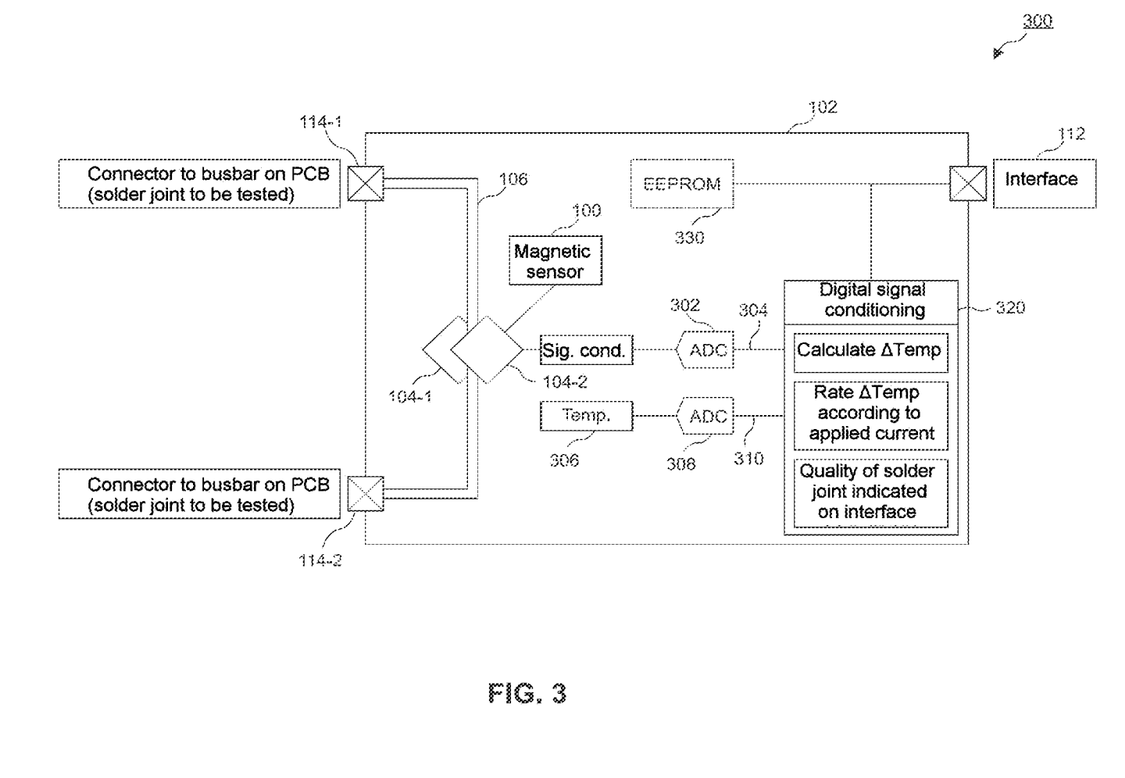
FIG. 3 shows an example of an apparatus for checking at least one solder joint between a printed circuit board and a current sensor.

FIG. 3 shows a block diagram of an apparatus 300 for checking at least one solder joint between a printed circuit board and a current sensor according to an exemplary embodiment.

As FIG. 3 shows, the apparatus 300 can be accommodated in a sensor package 102 that houses a magnetic field sensor chip or current sensor 100. The current sensor 100 can comprise differential Hall sensor elements 104-1, 104-2 arranged above, below or beside an internal current-carrying line 106. It will be obvious to a person skilled in the art that other sensor techniques, such as for example magnetoresistive sensor techniques, could also be used. The apparatus 300 can comprise connection pads 114-1, 114-2, in order to connect the internal current-carrying line 106 to an external current-carrying line by means of a solder joint (that is to be tested). The current sensor 100 can be used to measure an electric current through the solder joint and the internal current-carrying line 106 and to provide an appropriate (digital) current measurement signal 304 at the output of an analog-to-digital converter (ADC) 302. The apparatus 300 further comprises a temperature sensor 306, in order to measure at least one temperature of the current sensor 100 as a function of the electric current through the solder joint or the internal current-carrying line 106. The temperature sensor 306 can be used to measure a temperature close to the current sensor 100 and to provide an appropriate (digital) temperature measurement signal 310 at the output of an ADC 308. It goes without saying that the temperature sensor 306 according to some exemplary embodiments can be arranged together with the current sensor 100 inside a common sensor package. Exemplary embodiments in which the temperature sensor 306 is arranged outside the sensor package 102 are likewise possible, however. Furthermore, exemplary embodiments are conceivable in which the current and temperature sensors share an ADC, which, to that end, can be operated in multiplex mode, for example. The output of analog signals and external rating of the current and of the temperature rise are also conceivable.

The apparatus 300 further comprises a processor 320 designed to ascertain a quality of the solder joint based on the current measurement signal 304 and the temperature measurement signal 310. It goes without saying that the processor 320 according to some exemplary embodiments can be arranged together with the current sensor 100 inside a common sensor package. Exemplary embodiments in which the processor 320 is arranged outside the sensor package are likewise possible, however. The current intensity and duration of an electric current impressed (applied) via the connection pads 114-1, 114-2 can be predetermined for the checking of the solder joint. This means that the electric current is impressed at a predefined current intensity through the internal current-carrying line 106 regardless of the quality of the solder joint. This can be measured and checked by means of the current sensor 100.

As has already been illustrated with reference to FIG. 2C, different qualities of the solder joint lead to different temperatures in the sensor package 102 for a predetermined current. Therefore, in some exemplary embodiments, a temperature measurement signal 310 can provide information about the conductivity and hence the quality of the solder joint at the end of a measurement cycle. The higher the temperature rise for a specific current value, the poorer the conductivity and hence the quality of the solder joint. The temperature measured for the predefined current intensity could be compared for example with temperatures stored for the predefined current intensity and for different solder joint qualities in an optional memory 330 (for example an EEPROM) beforehand, and this could provide information about the quality of the solder joint.

Instead of just a final temperature at the end of a measurement cycle, it is preferably also possible for a temperature gradient to be ascertained and for the quality of the solder joint to be ascertained based on the temperature gradient and the electric current, in order to be able to rule out peripheral influences and to have the direct correlation with the current intensity. In order to determine the temperature gradient, a first temperature of the current sensor can be measured before the electric current is impressed, and a second temperature of the current sensor can be measured at the end of the electric current being impressed. The temperature gradient can then be ascertained based on the first temperature $T_1$, the second temperature $T_2$ and a period of time $\Delta t$ for which the electric current is impressed (temperature gradient=$(T_2-T_1)/\Delta t$). The temperature gradient ascertained for the predefined current intensity can then be compared for example with temperature gradients stored for the predefined current intensity and for different solder joint qualities in an optional memory 330 beforehand, and this can provide information about the quality of the solder joint.

The current sensor apparatus 300 measures the current or the magnetic field in the busbar. Additionally, the internal temperature is also measured. This temperature information can be used to check the temperature response as a function of a current. On the basis of simulation and measurement data stored in the memory 330, the dependency of the temperature gradient on a primary current and the percentage of solder cavities is known.

Figure 4:
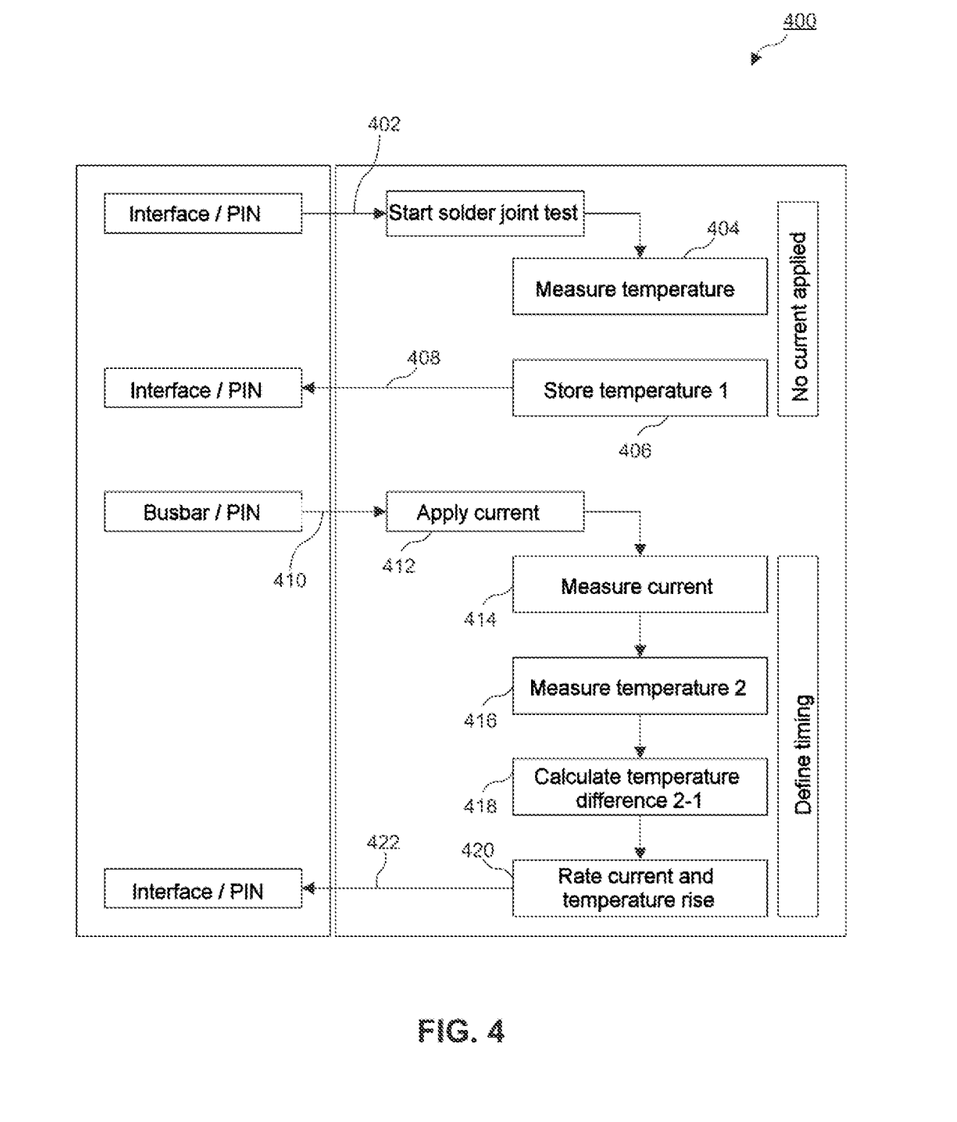
FIG. 4 shows an example of a method for checking at least one solder joint between a printed circuit board and a current sensor.

Using the interface 112, the result of the quality ascertainment can be communicated to an external processor. In a simple embodiment, the result can take on a binary appearance in the form "pass" ("1"), "fail" ("0"). Additionally, the current sensor apparatus 300 can receive commands via the interface 112, such as for example that a test on the solder joint is supposed to be carried out. A possible method sequence in this regard is shown in FIG. 4.

A first command 402 conveyed to the current sensor apparatus 300 from the outside via the interface 112 triggers a start for the method 400 for checking the solder joint between the printed circuit board and the current sensor apparatus 300 on the current sensor apparatus 300. This involves a first temperature $T_1$ of the current sensor apparatus 300 close to the current sensor 100 first of all being measured at 404 before an electric current is impressed. The measured temperature $T_1$ is buffer-stored at 406 and a signal 408 is output by the current sensor apparatus 300 (optionally to the outside) via the interface 112, in order to signal the ascertainment of the first temperature $T_1$. Preferably, the measuring of the temperature 404, in common with the optional storage 406 of the first temperature, is performed without (power) current applied to the current sensor, this being indicated by the box "No current applied" for steps 404 and 406 in FIG. 4. When recording the temperature gradient, it is necessary to take an initial temperature measurement 404. In this instance, either no current can flow through the busbar or a current whose RMS value differs from the current after the initial temperature measurement. The control and application of the current can be controlled from the outside. In an application with changing current values, the evaluation process (algorithm) can also be carried out autonomously without external control.

As FIG. 3 shows, the busbar 122 and the connection pads 114 are used at 410, 412 to impress an electric current into the internal line 106 at predetermined current intensity and over a predetermined period of time $\Delta t$. The electric current is measured at 414 by means of the current sensor 100. At the end of the measurement cycle, a second temperature $T_2$ is measured by means of the temperature sensor 306 at 416. At 418, a temperature rise $(T_2-T_1)$ and possibly a current rise is then ascertained. This information can then be evaluated at 420 and the result 422 of the solder point quality ascertainment can be transmitted to the outside by the current sensor apparatus 300 via the interface 112. It goes without saying that steps 418 and 420 could also be performed by an external processor.

The exemplary embodiments described with reference to FIGS. 3 and 4 make use of one or more internal memories in order to store the temperature $T_1$ for calculating the temperature gradient and the current values (magnetic field values), in order also to check a bounding window for the current (magnetic field). Additionally, there can be provision for an internal memory for storing the lookup table or the preset values for temperature and current. There is provision for an internal state machine, in order to compare the measured and stored values with stored limit values. The interface 112 can be used to set the limit values and to indicate the calculated solder point status.

Since a poor conductivity on account of poor solder joint quality leads to a higher power loss in the measurement path, the power loss can be identified by the proposed concept by virtue of an increased temperature rise in the sensor being recorded, as discussed in connection with FIG. 2C. The measurement of the current flowing through the sensor and the measurement of the temperature gradient in the device or package can involve the power loss being rated by an algorithm that takes into consideration both pieces of information. On the basis of a current-dependent thermal rating in a sensor package, a useful statement can be made about the quality of the solder point or the conductivity. The information about the quality of the solder point can be forwarded from the device to its surroundings.

The aspects and features described together with one or more of the examples and figures described in detail above can also be combined with one or more of the other examples in order to replace an identical feature of the other example or in order to introduce the feature into the other example in addition.

Examples can furthermore be or relate to a computer program having a program code for carrying out one or more of the above methods when the computer program is executed on a computer or processor. Steps, operations or processes from various methods described above can be carried out by programmed computers or processors. Examples can also cover program memory apparatuses, for example digital data storage media, that are machine, processor or computer readable and encode machine executable, processor executable or computer executable programs from instructions. The instructions carry out some or all of the steps of the methods described above or cause them to be carried out. The program memory apparatuses can comprise or be for example digital memories, magnetic storage media such as for example magnetic disks and magnetic tapes, hard disk drives or optically readable digital data storage media. Further examples can also cover computers, processors or control units programmed to carry out the steps of the methods described above, or (field) programmable logic arrays ((F)PLAs) or (field) programmable gate arrays ((F)PGAs) programmed to carry out the steps of the methods described above.

The description and drawings present only the principles of the disclosure. Furthermore, all examples mentioned here are intended to be used expressly only for illustrative purposes, in principle, in order to assist the reader in understanding the principles of the disclosure and the concepts contributed by the inventor(s) for further development of the art. All statements herein regarding principles, aspects and examples of the disclosure and also concrete examples thereof encompass the counterparts thereof.

A function block referred to as "means for . . . " carrying out a specific function can relate to a circuit designed for carrying out a specific function. Consequently, a "means for something" can be implemented as a "means designed for or suitable for something", for example a component or a circuit designed for or suitable for the respective task.

Functions of different elements shown in the figures, including any function blocks referred to as "means", "means for providing a signal", "means for generating a signal", etc., can be implemented in the form of dedicated hardware, e.g. "a signal provider", "a signal processing unit", "a processor", "a controller", etc. and as hardware capable of executing software in conjunction with associated software. When provided by a processor, the functions can be provided by a single dedicated processor, by a single jointly used processor or by a plurality of individual processors, some or all of which can be used jointly. However, the term "processor" or "controller" is far from being limited to hardware capable exclusively of executing software, but rather can encompass digital signal processor hardware (DSP hardware), network processor, application specific integrated circuit (ASIC), field programmable gate array (FPGA), read only memory (ROM) for storing software, random access memory (RAM) and nonvolatile memory apparatus (storage). Other hardware, conventional and/or customized, can also be included.

A block diagram can depict for example a rough circuit diagram that implements the principles of the disclosure. In a similar manner, a flow diagram, a flowchart, a state transition diagram, a pseudo code and the like can represent various processes, operations or steps that are represented for example substantially in a computer-readable medium and are thus performed by a computer or processor, regardless of whether such a computer or processor is explicitly shown. Methods disclosed in the description or in the patent claims can be implemented by a component having a means for performing each of the respective steps of said methods.

It goes without saying that the disclosure of multiple steps, processes, operations or functions disclosed in the description or the claims should not be interpreted as being in the specific order, unless this is explicitly or implicitly indicated otherwise, for example for technical reasons. The disclosure of multiple steps or functions therefore does not limit them to a specific order unless said steps or functions are not interchangeable for technical reasons. Further, in some examples, an individual step, function, process or operation can include multiple partial steps, functions, processes or operations and/or be subdivided into them. Such partial steps can be included and be part of the disclosure of said individual step, provided that they are not explicitly excluded.

Furthermore, the claims that follow are hereby incorporated in the detailed description, where each claim can be representative of a separate example by itself. While each claim can be representative of a separate example by itself, it should be borne in mind that—although although a dependent claim can refer in the claims to a specific combination with one or more other claims—other examples can also encompass a combination of the dependent claim with the subject matter of any other dependent or independent claim. Such combinations are explicitly proposed here, provided that no indication is given that a specific combination is not intended. Furthermore, features of a claim are also intended to be included for any other independent claim, even if this claim is not made directly dependent on the independent claim.

What is claimed is:

1. A method for evaluating a quality of a solder joint connected between a printed circuit board and a current-carrying line, comprising:
   applying, by a current source, an electric current to flow through the solder joint and the current carrying line electrically connected to the solder joint;
   measuring, by a current sensor, the electric current that flows through the solder joint;
   measuring, by a temperature sensor, a temperature of the current sensor as the electric current flows through the solder joint;
   ascertaining, by a processing circuit, the quality of the solder joint based on the measured temperature and the measured electric current; and
   generating, by the processing circuit, a signal indicative of the quality of the solder joint.

2. The method as claimed in claim 1, wherein the temperature is measured by means of the temperature sensor integrated in the current sensor.

3. The method as claimed in claim 1, wherein a current intensity and a duration of the electric current are predetermined for checking of the solder joint.

4. The method as claimed in claim 1, wherein:
   measuring of the temperature comprises measuring of a temperature gradient, and
   the quality of the solder joint is ascertained based on the measured temperature gradient and the measured electric current.

5. The method as claimed in claim 4, wherein a first temperature of the current sensor is measured before the electric current is impressed, and a second temperature of the current sensor is measured at an end of the electric current being impressed, and wherein the temperature gradient is ascertained based on the first temperature, the second temperature, and a period of time for which the electric current is impressed.

6. The method as claimed in claim 1, wherein ascertaining of the quality of the solder joint comprises comparing the measured temperature with reference temperatures ascertained for the electric current at different solder joint qualities.

7. The method as claimed in claim 1, wherein the quality of the solder joint is ascertained by means of a processor integrated with the current sensor.

8. The method as claimed in claim 1, wherein the measured electric current and the measured temperature are conveyed from the current sensor to the processing circuit via an interface, and the processing circuit is configured to ascertain the quality of the solder joint based on the measured electric current and the measured temperature.

9. The method as claimed in claim 1, wherein the current sensor comprises at least one Hall sensor or a magnetoresistive sensor.

10. The method as claimed in claim 1, further comprising:
    storing, in a look up table stored in memory, different levels of solder joint qualities, each correlated to one or more different combinations of temperature and electric current; and
    determining, by the processing circuit, one of the different levels of solder joint qualities as the quality of the solder joint based on the measured temperature and the measured electric current.

11. The method as claimed in claim 1, further comprising:
    selecting, by the processing circuit, a temperature threshold from a plurality of temperature thresholds stored in memory based on the measured electric current;
    comparing, by the processing circuit, the measured temperature to the selected temperature threshold;
    determining, by the processing circuit, that the quality of the solder joint has a first quality level if the measured temperature is less than or equal to the selected temperature threshold; and determining, by the processing circuit, that the quality of the solder joint has a second quality level if the measured temperature is greater than the selected temperature threshold.

12. The method as claimed in claim 1, further comprising:
measuring, by the processing circuit, a temperature gradient of the current sensor over a measurement period while the electric current flows through the solder joint during the measurement period; and
ascertaining, by the processing circuit, the quality of the solder joint based on the measured temperature gradient and the measured electric current.

13. The method as claimed in claim 1, further comprising:
storing, in a look up table stored in memory, different levels of solder joint qualities correlated to different combinations of temperature gradients and predetermined current intensities;
applying, by the current source, the electric current with a predetermined current intensity;
measuring, by the processing circuit, a temperature gradient of the current sensor over a measurement period while the electric current flows through the solder joint at the predetermined current intensity during the measurement period; and
determining, by the processing circuit, one of the different levels of solder joint qualities as the quality of the solder joint based on the measured temperature gradient and the predetermined current intensity of the applied electric current.

14. The method as claimed in claim 1, further comprising:
applying, by the current source, the electric current with a predetermined current intensity for a predetermined period; and
measuring, by the processing circuit, a temperature gradient of the current sensor by measuring a first temperature of the current sensor substantially at a start of the predetermined period, measuring a second temperature of the current sensor substantially at an end of the predetermined period, and determining the temperature gradient based on the first temperature, the second temperature, and a length of the predetermined period.

15. The method as claimed in claim 1, further comprising:
applying, by the current source, the electric current with a predetermined current intensity for a predetermined period; and
measuring, by the processing circuit, a temperature gradient of the current sensor by measuring a first temperature of the current sensor at a first sampling time, measuring a second temperature of the current sensor at a second sampling time subsequent to the first sampling time, and determining the temperature gradient based on the first temperature, the second temperature, and the predetermined period.

16. The method as claimed in claim 15, wherein the first sampling time is triggered prior to applying the electric current with the predetermined current intensity and the second sampling time is triggered during the predetermined period for which the electric current with the predetermined current intensity is applied.

17. The method as claimed in claim 16, wherein the second sampling time is triggered at an end of the predetermined period.

18. The method as claimed in claim 1, wherein the quality of the solder joint is a measure of a conductivity of the solder joint.

19. The method as claimed in claim 1, further comprising:
determining, by the processing circuit, whether the quality of the solder joint passes or fails a quality standard; and
generating, by the processing circuit, the signal indicating whether the quality of the solder joint passes or fails the quality standard.

20. A system, comprising:
a printed circuit board;
a current sensor configured to measure an electric current;
a solder joint connected between the printed circuit board and a current-carrying line, wherein the electric current flows through the solder joint and the current-carrying line;
a temperature sensor configured to measure a temperature of the current sensor as the electric current flows through the solder joint; and
a processor coupled to the current sensor for receiving a current measurement of the electric current therefrom and coupled to the temperature sensor for receiving a temperature measurement of the temperature therefrom, wherein the processor is configured to receive the current measurement, the temperature measurement, and ascertain a quality of the solder joint based on the temperature measurement and the current measurement.

21. The system as claimed in claim 20, wherein the processor is external to the current sensor, and the current sensor and the processor are coupled via a signal interface for transmitting signals that indicate the measurement of the measured temperature and the measurement of the measured electric current.

22. The system as claimed in claim 20, wherein the processor and the current sensor form an integrated circuit.

23. A method for evaluating a quality of a solder joint connected between a printed circuit board and current-carrying line arranged proximate to a current sensor, the method comprising:
applying, by a current source, an electric current with a predetermined current intensity to flow through the solder joint and the current carrying line electrically connected to the solder joint for a predetermined period;
measuring, by a processing circuit cooperatively coupled to a temperature sensor, a temperature gradient of the current sensor as the electric current flows through the solder joint by measuring a first temperature of the current sensor at a first sampling time at which time a current intensity of the electric current differs from the predetermined current intensity, measuring a second temperature of the current sensor at a second sampling time at which time the electric current has the predetermined current intensity, and determining the temperature gradient based on the first temperature and the second temperature; and
ascertaining, by the processing circuit, a quality of the solder joint based on the measured temperature gradient and the predetermined current intensity.

* * * * *

UNITED STATES PATENT AND TRADEMARK OFFICE
CERTIFICATE OF CORRECTION

PATENT NO. : 11,513,090 B2
APPLICATION NO. : 16/993544
DATED : November 29, 2022
INVENTOR(S) : Theodor Kranz It is certified that error appears in the above-identified patent and that said Letters Patent is hereby corrected as shown below:

In the Claims

Claim 20:
Column 12, Line 26, change "current measurement, the temperature measurement," to --current measurement and the temperature measurement,--

Signed and Sealed this
Third Day of January, 2023

Katherine Kelly Vidal
*Director of the United States Patent and Trademark Office*